(12) United States Patent
Kuret et al.

(10) Patent No.: US 6,479,528 B1
(45) Date of Patent: Nov. 12, 2002

(54) METHODS FOR INHIBITING OR REVERSING TAU FILAMENT FORMATION POLYMERIZATION

(75) Inventors: Jeff Kuret, Dublin, OH (US); Sam Khatami, Highland Park, IL (US)

(73) Assignee: Neuronautics, Inc., Evanston, IL (US)

( * ) Notice: Subject to any disclaimer, the term of this patent is extended or adjusted under 35 U.S.C. 154(b) by 0 days.

(21) Appl. No.: 09/919,508

(22) Filed: Jul. 31, 2001

(51) Int. Cl.[7] ............ A61K 31/425; A61K 31/40; A61K 31/38; A61K 31/195
(52) U.S. Cl. ............ 514/367; 514/418; 514/447; 514/566
(58) Field of Search ............ 514/367, 418, 514/447, 566

(56) References Cited

U.S. PATENT DOCUMENTS

6,001,331 A * 12/1999 Caprathe et al. ............ 424/9.1

\* cited by examiner

*Primary Examiner*—William R. A. Jarvis
(74) *Attorney, Agent, or Firm*—Fitch, Even, Tabin & Flannery (57) ABSTRACT

Methods for inhibiting and/or reversing tau filament formation or polymerization are provided. These methods can be used for treating certain neurological disorders in vivo by administering pharmaceutical compositions which inhibit and/or reverse tau filament formation or polymerization. An especially preferred pharmaceutical composition contains an inhibitor of the general formula I

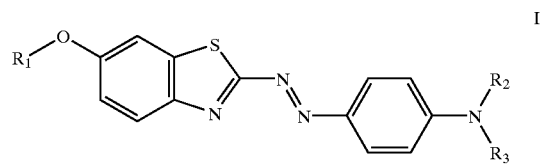

wherein $R_1$ is an aliphatic radical having one to six carbon atoms and wherein $R_2$ and $R_3$ independently are a second aliphatic radical having one to six carbon atoms, a hydroxyl-substituted aliphatic radical having one to six carbon atoms, or a pheny radical or a pharmaceutically acceptable salt of the inhibitor.

22 Claims, 3 Drawing Sheets

METHODS FOR INHIBITING OR REVERSING TAU FILAMENT FORMATION POLYMERIZATION

FIELD OF THE INVENTION

The current invention relates to methods for inhibiting and/or reversing tau filament formation or polymerization. This invention also relates to methods for treating certain neurological disorders in vivo by administering pharmaceutical compositions which inhibit and/or reverse tau filament formation or polymerization.

BACKGROUND

The microtubule-associated protein tau is a soluble cytosolic protein that is believed to contribute to the maintenance of the cytoskeleton (Johnson et al., *Alzheimer's Disease Review* 3: 125 (1998); Buee et al., *Brain Research Reviews* 33:95 (2000)). However, in many disease states, tau protein is induced by unknown cellular conditions to self-associate into filamentous structures (Spillantini et al., *Trends Neurosci.* 21: 428 (1998)). These filamentous forms of tau can be found in such varied neurodegenerative disorders as Alzheimer's disease (AD) (Wood et al., *Proc. Natl. Acad. Sci. USA* 83: 4040 (1986); Kosik et al., *Proc. Natl. Acad. Sci. U.S.A* 83: 4044 (1986); Grundke-Iqbal et al., *J. Biol. Chem.* 261: 6084 (1986)), corticobasal degeneration (CBD) (Feany et al., *Am. J. Pathol.* 146: 1388 (1995)), progressive supranuclear palsy (PSP) (Tabaton et al., *Ann. Neurol.* 24: 407 (1988)), Pick's disease (PD) (Murayama et al., *Ann. Neurol.* 27: 394 (1990)), Down syndrome (Papasozomenos et al., *Lab Invest.* 60: 123 (1989)), and frontotemporal dementias and Parkinsonism linked to chromosome 17 (FTDP-17) (Spillantini et al., *Proc. Natl. Acad. Sci. USA* 94: 4113 (1997)). There remains a need for the identification of effective therapies for these neurodegenerative disorders.

There is still debate as to the involvement of tau fibril formation in the onset of neurodegeneration. It is not known whether abnormal tau polymerization causes or modulates the neurodegeneration process or whether it is simply a byproduct of the process. For example, in AD it is hotly debated whether the dementia-causing pathological structures are the amyloid-beta positive senile plaques, the tau-positive neurofibrillary tangles, or a combination of both (Hardy et al., *Nat. Neurosci.* 1: 355 (1998)). In order to understand the etiopathogenesis of AD, there remains a need to identify molecular mechanisms which lead to the polymerization of the pathological structures themselves.

Much of what is currently known regarding tau polymerization stems from in vitro assembly assays. However, with few exceptions, the conditions that have been used to achieve tau polymerization have been extremely nonphysiological. The first experiment describing the self-association of tau protein into AD-like filaments involved 60 hours of incubation in 8M urea (Montejo de Garcini et al., *J. Biochem.* (Tokyo) 102: 1415 (1987)). Other experiments have required significant truncations of the molecule followed by chemical cross-linking (Wille et al., *J. Cell. Biol.* 118: 573 (1992)), extremely high protein concentrations (40 μM) (Goedert et al., *Nature* 383: 550 (1996)), incubation periods up to six weeks (Schweers et al., *Proc. Natl. Acad. Sci. USA* 92: 8463 (1995)), or combinations of these techniques. Although relatively mild conditions have been described which result in the polymerization of low concentrations of biochemically purified tau protein (Wilson et al., *J. Biol. Chem.* 270: 24306 (1995)), this process can be greatly enhanced by the addition of polyanionic compounds under oxidative conditions (Goedert et al., *Nature* 383: 550 (1996); Kampers et al., *FEBS Lett.* 399: 344 (1996); Hasegawa et al., *J. Biol. Chem.* 272: 33118 (1997); Friedhoff et al., *Biochemistry* 37: 10223 (1998); Friedhoff et al., *Proc. Natl. Acad. Sci. USA* 95: 15712 (1998); Nacharaju et al., *FEBS Lett.* 447: 195 (1999)) and the addition of free fatty acids under reducing conditions (Nacharaju et al., *FEBS Lett.* 447: 195 (1999); Wilson et al., *Am. J. Pathol.* 150: 2181 (1997); King et al., *Biochemistry* 38: 14851 (1999); King et al., *J. Neurochem.* 74: 1749 (2000); Gamblin. et al., *Biochemistry* 39: 6136 (2000)). However, there remains a need to identify improved methods for further enhancing the polymerization of tau protein in vitro in order to help facilitate the identification of reagents which can be used to treat diseases involving tau polymerization in vivo.

Various in vitro polymerization techniques have been used to investigate the in vitro polymerization of tau. For example, it has been shown that the fatty acid induction of tau polymerization proceeds through a ligand-dependent mechanism under reducing conditions (King et al., *Biochemistry* 38: 14851 (1999)). Another set of experiments showed that, contrary to expectations, extensive phosphorylation of the tau molecule with various protein kinases inhibited the polyanion induction of polymerization (Schneider et al., *Biochemistry* 38: 3549 (1999)). Some of the factors leading to tau polymerization in the disease state are now being studied. As mentioned above, extensive tau pathology is observed in a class of neurodegenerative disorders called FTDP-17. These disease states have been linked to mutations in the tau gene that lead to missense point mutations or changes in the isoform expression of the tau protein. In vitro experiments have shown that several of the single amino acid missense point mutations found in FTDP-17 can lead to increased filament formation (Nacharaju et al., *FEBS Lett.* 447: 195 (1999); Gamblin et al., *Biochemistry* 39: 6136 (2000); Goedert et al., *Nat. Med.* 5: 454 (1999)). It has also been shown that tau isoforms have different polymerization characteristics, which could lead to increased tau pathology in cases of FTDP-17 with altered isoform compositions (King et al., *J. Neurochem.* 74: 1749 (2000)). However, a strong link between the risk factors associated with the most common neurodegenerative disorder, AD, and increased tau polymerization has not been established. Therefore, there remains a need to identify AD risk factors that are associated with tau polymerization in order to accelerate the development of effective AD therapies.

A number of risk factors have been identified which have the common characteristic of being potential contributors to oxidative stress. Thus, oxidative stress may play a major role in the etiology of Alzheimer's disease (AD). The normal aging process, head trauma, increased levels of heavy metals (e.g., Fe, Al, Hg), and, especially in the case of AD, aggregation of the β-amyloid protein (Aβ) are all thought to be potential contributors to increased oxidative stress. In the oxidative stress hypothesis for AD, free radicals generated by these risk factors, possibly in the form of reactive oxygen species, would then attack biological molecules that are sensitive to oxidation, such as proteins, DNA, and lipids/fatty acids, causing a cascade that would eventually lead to neurodegeneration (see, e.g., Markesbery et al., *Free Radic. Biol. Med.* 23: 134 (1997)).

There is direct evidence that sensitive molecules in vulnerable AD brains are modified by oxidative stress. Free radicals can lead to the carbonyl derivatization of enzymes such as glutamine synthetase and creatine kinase. This process is quickly followed by protease degradation of the enzymes. DNA is also sensitive to oxidative stress. Increases in the adduct 8-hydroxy-2'-deoxyguanisine have been reported for mitochondrial DNA, and to a lesser extent nuclear DNA, in AD brains when compared to age-matched controls. In addition, a two-fold increase in oxidative damage to DNA through strand breaks has been described in the brains of AD patients (see, e.g., Markesbery et al., *Free Radic. Biol. Med.* 23:134 (1997)).

Polyunsaturated fatty acids (FA) are especially vulnerable to oxidative stress since their double bonds make the removal of H+ by free radicals relatively easy. Although some reports disagree on the location of FA oxidation in AD brain (see, e.g., Markesbery, *Brain Pathol.* 9: 133 (1999)), it is clear that thiobarbituric acid reactive substances (a marker for FA oxidation) are elevated in these patients. In addition, many FA breakdown products including malondialdehyde (MDA) and hydroxynonenal (HNE) can be detected at greater than normal levels in AD patients. Increased amounts of specific FA metabolites, such as the F2-isoprostanes and F4-neuroprostanes, can also be found in the affected brain regions of AD patients and even in the cerebrospinal fluid of probable AD patients (Montine et al., *Neurology* 52: 562 (1999)). In addition to the toxicity of some of the FA breakdown products (such as HNE), the alterations in membrane fluidity as a result of FA oxidation may also have deleterious effects in AD patients.

While it is becoming clear that oxidative stress is likely a significant contributor to the neurodegenerative process, it is not clear how these factors are related to the two major pathological structures found in AD, senile plaques and neurofibrillary tangles. Senile plaques (SPs), which consist mainly of polymerized Aβ protein, may contribute to oxidative stress though the generation of free radicals, but their involvement in the neurodegenerative process is not clear. While the addition of Aβ to cultured neurons results in increased protein oxidation and cell death (Busciglio et al., *Neuron* 14: 879 (1995)), animal models that contain elevated amounts of SPs do not show signs of neurodegeneration (Takeuchi et al., *Am. J. Pathol.* 157: 331 (2000)). In addition, the presence of SPs does not correlate well with the degree of dementia in AD patients (Arriagada et al., *Neurology* 42: 631 (1992)).

In contrast, neurofibrillary tangles (NFTs) consisting primarily of polymerized tau molecules do correlate well with the degree of dementia in AD (Arriagada et al., *Neurology* 42: 631 (1992)). In addition, an emerging class of neurodegenerative disorders that involve the fronto-temporal regions of the brain appear to be caused by pathological tau inclusions in the absence of SPs (Spillantini et al., *Proc. Natl. Acad. Sci. USA* 94: 4113 (1997)). Finally, the formation of tau filaments appears to directly cause neurodegeneration in an animal model. Overexpression of the tau protein in lamprey ABC neurons leads to filament formation and subsequent neuronal death (Hall et al., *Proc. Natl. Acad. Sci. USA* 94: 4733 (1997); Hall et al., *J. Cell Sci.* 113: 1373 (2000)).

Although the formation of NFTs may be relevant to the neurodegenerative process, it is not clear how they are involved with the oxidative stress hypothesis for AD. Previously, the only link between oxidative stress and tau filament formation has been the reports which describe the prerequisite oxidation of the tau molecule for its polymerization in vitro. The oxidation of a specific cysteine that results in disulfide-linked dimers of tau has been shown to be a necessary first step before the induction of tau filament formation (Schweers et al., *Proc. Natl. Acad. Sci. USA* 92: 8463 (1995)). It should be noted, however, that these results required special conditions to be effective. First, the experiments were performed on tau molecules truncated at both the amino- and carboxy-terminal regions so that only the microtubule binding repeat (MTBR) regions remained. Secondly, only three microtubule binding repeats could be used. This was due to the fact that there are two cysteines in the tau molecule, one in MTBR2 and one in MTBR3. If both cysteines were left in the tau constructs, they preferentially formed intramolecular disulfides instead of forming dimers.

The tau oxidation theory does not seem tenable for several reasons. The cellular markers for protein oxidation that have been identified in AD as a result of oxidative stress are the creation of protein carbonyls and the nitration of tyrosine residues (see, e.g., Markesbery et al., *Brain Pathol.* 9: 133 (1999)). It is not clear whether oxidative stress would actually result in the cysteine oxidation and subsequent dimerization of tau molecules. The filamentous tau structures found in AD consist of all six isoforms of the tau molecule, including those with four MTBR (see, e.g., Spillantini et al., *Trends in Neurosciences,* 21: 428 (1998)). Therefore, tau molecules containing two cysteines are capable of polymerizing in vivo. If cysteine oxidation of the tau molecule is a prerequisite and the intramolecular disulfide formation is favored over dimerization, one would not expect the four MTBR isoforms of tau to be present in the filaments that make up the NFTs. Therefore, there remains a need to determine the effects of oxidation on tau polymerization in vivo and the mechanism by which oxidative stress induces neurodegeneration in AD.

Using methods described in co-pending U.S. application Ser. No. 09/919,475, filed on the same date as the present application and based on U.S. Provisional Application Serial No. 60/221,777 filed on Jul. 31, 2000, specific relatively low molecular weight liqands (generally less than about 400 daltons) have been identified which inhibit and/or reverse tau filament formation or polymerization a substoichiometric concentrations relative to tau protomer. This co-pending application, which is owned by the same assignee of the present application, is hereby incorporated by reference. These liqands or inhibitors can be used therapeutically to treat certain neurological disorders or disease states in vivo, including Alzheimer's disease, in which tau filaments are formed.

SUMMARY OF THE INVENTION

In one embodiment, the present invention provides a method for regulating the assembly of the protein tau in the brain of a patient, comprises:

identifying a patient in need of a method for inhibiting tau polymerization in the brain; and administering to the patient a pharmacologically effective amount of an inhibitor of fatty acid oxidation, wherein the inhibitor is selected from the group consisting of (1) a first compound of the general formula

I wherein $R_1$ is an aliphatic radical having one to six carbon atoms and wherein $R_2$ and $R_3$ independently are a second aliphatic radical having one to six carbon atoms, a hydroxyl-substituted aliphatic radical having one to six carbon atoms, or a pheny radical; (2) a second compound of general formula

II wherein $R_4$, $R_6$, and $R_8$ are independently a third aliphatic radical having 1 to 6 carbon atoms and $R_5$ and $R_7$ are independently a fourth aliphatic radical having 1 to 6 carbon atoms or a second hydroxyl-substituted aliphatic radical having one to six carbon atoms; (3) a third compound of general formula

III (4) a fourth compound of general formula

IV wherein $R_9$ and $R_{10}$ independently are a fourth aliphatic radical having 1 to 6 carbon atoms; (5) a fifth compound of general formula

V wherein $R_{11}$ is a carboxylic acid-substituted aliphatic radical having 1 to 6 carbon atoms and $R_{12}$ is a fifth aliphatic radical having 1 to 6 carbon atoms; and (6) pharmaceutically acceptable salts thereof.

Preferably, the inhibitor is the first compound of the general formula

I wherein $R_1$ is an aliphatic radical having one to six carbon atoms and wherein $R_2$ and $R_3$ independently are a second aliphatic radical having one to six carbon atoms, a hydroxyl-substituted aliphatic radical having one to six carbon atoms, or a pheny radical. More preferably, the inhibitor is 2-[[4-(dimethylamino)phenyl]azo]-6-methoxylbenzothiazole (i.e., $R_1$, $R_2$, and $R_3$ are methyl groups in the above formula I) having the formula I':

I'

In one embodiment, the patient is a human. Generally the inhibitor is administered in an effective amount which can be determined using conventional techniques. Generally, the inhibitor is administered in an amount selected from about 10 mg per day to about 1000 mg per day. In one embodiment, the administering is performed repeatedly over a period of at least one week. In one embodiment, the administering is performed repeatedly over a period of at least one month. In one embodiment, the administering is performed repeatedly over a period of at least three months. In one embodiment, the administering is performed repeatedly over a period of at least one year. In another embodiment, the administering is performed at least once monthly. In another embodiment, the administering is performed at least once weekly. In another embodiment, the administering is performed at least once daily. In another embodiment, the administering is performed at least once weekly for at least one month. In another embodiment, the administering is performed at least once per day for at least one month.

BRIEF DESCRIPTION OF THE DRAWINGS

FIGS. 1(A, B, and C). Panel A: arachidonic acid-induced (75 mM) polymerization of recombinant human htau40 (8 mM) assayed (3.5 h; room temperature) in the presence of thioflavin S (4 mM) and varying concentrations (0, 3, 6, 12, 25, 50, 100, 200, 400, 800, 1600 nM) of 2-[[4-(dimethylamino)phenyl]azo]-6-methoxylbenzothiazole (compound I') using a fluorescence assay as described in the Example. Plots of % control (i.e., DMSO vehicle without compound I') fluorescence remaining versus compound I' concentration show that compound I' inhibits htau40 polymerization with an $IC_{50}$ of 54±6 nM. Panels B and C: electron microscopy assay as described in the Example and using htau40$^{C291A, C322A}$ as the source of tau at compound I' concentrations of 0 nM (Panel B) and 200 nM (Panel C) confirm that compound I' inhibits tau polymerization. Polymerization in the presence of 200 nM compound I' (1:40 molar ratio relative to tau) reduced total filament number and length to 14.2±0.6% and 20.2±0.7% of control values (mean±range of duplicates), respectively.

FIG. 2. This figure illustrates the disassembly of synthetic tau filaments. Filaments prepared from recombinant htau40 (4 mM) over 3 hours at room temperature were diluted 20-fold into polymerization buffer containing thioflavin S (2 mM) and either 4 mM htau40 (■), 75 mM arachidonic acid (●), or no additions (□). The resultant depolymerization was followed by thioflavin S fluorescence (F) over time. These data show that synthetic tau filaments require the presence of both tau protomer and arachidonic acid inducer for stability.

FIGS. 3(A and B). This figure shows the timecourse of compound I'-mediated depolymerization. Filaments prepared from 8 mM recombinant htau40$^{C291A,\ C322A}$ (100 mM arachidonic acid) for 3.5 hours at room temperature were further incubated in the presence of DMSO vehicle (■) or 200 nM compound I' (□) for 1 h. Aliquots of the reaction were stopped at 0, 10, 20, 30, 45, and 60 minutes by the addition of glutaraldehyde and filaments ≧50 nm in length analyzed by electron microscopy. Each data point represents top, total filament length per field and bottom, total number of filaments per field±standard deviation (n=5 observations). In the absence of compound I', tau filament formation continued toward equilibrium with small increases in total filament length (Panel A) and number of filaments (Panel B) >50 nm per field. In the presence of 200 nM compound I', however, total filament length per field decreased with an initial first order rate of 0.042 min-1 (top, solid line) and was accompanied by a slow decrease in the total number of filaments. After 1 hour incubation in the presence of 200 nM compound I', total filament number and length had decreased to 84±26% and 21±6% of that observed in vehicle only controls, respectively.

FIGS. 4(A and B). This figure illustrates length distribution of filaments during compound I'-mediated depolymerization. The relative length distributions of htau40$^{C291A,\ C322A}$ filaments ≧50 nm arising from the experiment shown in FIG. 3 were plotted in histogram form (bin size of 100 nm) 10 (□), 20 (●), 30 (○), 45 (▲), and 60 (△) minutes after addition of DMSO vehicle or 200 nM compound I'. Each data point represents the total filament length in a 100 nm-wide bin±standard deviation (n=5 observations). Panel A: in the presence of DMSO vehicle, htau40$^{C291A,\ C322A}$ filaments maintain an exponential distribution of lengths that changes little over 1 hour incubation time. Panel B: in the presence of 200 nM compound I', the exponential distribution of filament lengths is maintained after 10 (□), 20 (●), 30 (○), and 60 (△) min incubation but shifts to shorter filament lengths. For comparison, each panel shows the initial length distribution at time 0 (■).

FIG. 5. This figure illustrates small molecule-mediated disassembly of authentic tau filaments. Tau filaments isolated from AD brain (0.03 mg/ml) were incubated 20 min in the presence of (■) DMSO vehicle or (□) 2 mM compound I'. Aliquots of the reaction were stopped after 0, 10, and 20 min incubation by the addition of glutaraldehyde and filaments ≧50 nm in length analyzed by electron microscopy. Each data point represents total filament length per field±standard deviation (n=5). After 20 min incubation with compound I', total filament length was only 14±9% of that of the DMSO vehicle control.

DESCRIPTION OF THE PREFERRED EMBODIMENTS

The current invention is a method for regulating the assembly of the protein tau in the brain of a mammal in need of such a regulation, wherein the method comprises administering to the mammal a pharmacologically effective amount of an inhibitor of fatty acid oxidation in a pharmaceutically-acceptable carrier. For purposes of this invention, the term "regulating the assembly of the protein tau" includes, but is not limited to, inhibiting and/or reversing tau filament formation or polymerization and/or moderating the rate of tau filament formation or polymerization.

Tau protein assembles into linear filaments capable of binding histochemical dyes such as Congo Red and thioflavin S, suggesting it polymerizes with the extended beta sheet conformation characteristic of "amyloid" deposits (Rochet et al., Cur. Op. Struct. Biol. 10: 60 (2000); Serpell et al., J. Mol. Biol. 300:1033 (2000)). On the basis of ligand-mediated assembly reactions conducted in vitro with both fragmentary and full-length tau protein, polymerization is mediated by a short hydrophobic sequence located in its microtubule repeat region (von Bergen et al., Proc. Natl. Acad. Sci. USA 97: 5129 (2000); Abraha et al., J. Cell Sci. 113: 3737 (2000)). However, sequences outside this region have a striking effect on both the kinetics of polymerization and the organization of protomers within the filament (Abraha et al., J. Cell Sci. 113: 3737 (2000); Gianetti et al., Protein Sci. 9: 2427 (2000)). Thus, despite retaining general similarity with amyloid fibrils derived from other proteins, filaments of full-length tau protein offer potentially unique pharmacophores for binding polymerization inhibitors.

The azo dye 2-[[4-(dimethylamino)phenyl]azo]-6-methoxylbenzothiazole (compound I'), as well as similar compounds, has been found to inhibit fatty-acid mediated formation of straight filaments from purified, recombinant htau40. Unlike thiazin derivatives described previously (Wischik et al., Proc. Natl. Acad. Sci. USA 93: 11213 (1996)), 2-[[4-(dimethylamino)phenyl]azo]-6-methoxylbenzothiazole (compound I') inhibited tau polymerization by 50% at concentrations below 100 nM and substoichiometric with respect to tau protomer. Compound I' also promoted disassembly of mature synthetic straight filaments under these conditions. Authentic paired helical filaments from AD brain were also destabilized by micromolar concentrations of compound I'. In addition to its potency, compound I' has an advantage over other amyloid inhibitors (Findeis, Biochim. Biophys. Acta 1502: 76 (2000)) by being uncharged at physiological pH, which will facilitate pharmacological dissection of tau polymerization activity in intact cells.

For compound I' acting on tau fibrils, disaggregation activity is expressed at filament ends, which are present at much lower concentration than tau protomer. In support of this conclusion, it was found that compound I'-mediated disassembly proceeded at subtoichiometric concentrations and followed first order kinetics while maintaining a near exponential distribution of filament lengths. Moreover, the decrease in filament number accompanying compound I'-mediated depolymerization was consistent with progressive endwise depolymerization and inconsistent with catastrophic filament breakage along the filament length. Although not wishing to be limited by theory, this inhibitory pattern may derive from any of three general mechanisms. First, compound I' may interfere with the arachidonic acid used to promote tau polymerization in vitro. In addition to promoting assembly, dilution experiments confirmed the importance of fatty acid for maintaining filament stability. This mechanism appears unlikely, however, because the $IC_{50}$ for compound I' was <0.1% the molar concentration of arachidonic acid, and because compound I' drove the disassembly of authentic filaments where no fatty acid was present. Second, compound I' may bind to tau monomers forming a complex that does not support fibril formation. This mechanism has been invoked for the inhibition of polymerization of globular protomers, such as transthyretin by stoichiometric concentrations of flufenamic acid or tubulin by substoichiometric concentrations of colchicine (Peterson et al., *Proc. Natl. Acad. Sci. USA* 95: 12956 (1998); Skoufias et al., *Biochemistry* 31: 738 (1992)). In the latter example, substoichiometric inhibition of polymerization and promotion of disassembly depends upon filament polarity, where assembly and drug action occur primarily at one end while disassembly proceeds at the opposite end (Perez-Ramirez et al., *Biochemistry* 35: 3277 (1996)). Because seeding experiments are consistent with tau filaments having growth polarity (King et al., *Biochemistry* 38: 14851 (1999)), this mechanism cannot be ruled out at present. Nonetheless, monomeric tau protein has limited ordered structure in solution, and so a third possibility is that the receptor for compound I' at low concentration may actually be the extended beta sheet structure of fibrils as proposed for Congo Red (Klunk et al., *J. Histochem. Cytochem.* 37: 1273 (1989)). Like compound I', Congo Red is a planar aromatic azo dye, and on the basis of its stoichiometry of binding and optical properties (birefringence) is thought to bind all along the length of amyloid fibrils (Klunk et al., (1989)). Although binding of macromolecules along the length of amyloid fibrils can lead to disaggregation (Fraser et al., *J. Neurochem.* 61: 298 (1993); Solomon et al., *Proc. Natl. Acad. Sci. USA* 94: 4109 (1997)), similar binding of small organic dyes like Congo Red does not necessarily do so (Ashburn et al., *Chem. Biology* 3: 351 (1996)). For example, the concentration of thioflavin S (a fluorescent dye structurally similar to Congo Red) required for binding synthetic tau filaments ($EC_{50} \approx 1$ mM; King et al., 1999) is not sufficient to inhibit or reverse tau polymerization. Similarly, compound I' at concentrations required to bind synthetic $A\beta_{1-40}$ filaments ($EC_{50}=3.2$ mM; Caprathe et al., U.S. Pat. No. 6,001,331 (Dec. 14, 1999)) does not interfere with $A\beta_{1-40}$ assembly. In contrast, Ro 90-7501 (an analog of thioflavin S; Bohrmann et al., *J. Struct. Biol.* 130: 232 (2000)) and compound I' inhibit polymerization and promote disaggregation of Ab and tau fibrils, respectively. These data suggest that the binding sites on amyloid filaments that host compound I' and other dyes may be heterogeneous (LeVine, *Arch. Biochem. Biophys.* 342: 306 (1997)), with sites located at filament ends having differerent properties form those appearing along the length of the fibril. In this case, direct binding to one or both filament ends may block further addition of tau, leading to unopposed or even accelerated dissociation of tau protomers. Additional binding of compound I' along the filament length may or may not influence inhibition occurring at filament ends. It cannot be ruled out, however, that all dye binding sites on a fibril are homogeneous, and that only certain ligands such as compound I' alter protomer conformation sufficiently to promote disaggregation.

The inhibitory properties of compound I' described herein were determined with synthetic straight filaments prepared from recombinant full-length tau that on the basis of morphology and protomer stoichiometry correspond to one hemifilament of the PHF (King et al., 1999; King et al., *Am. J. Pathol.* 158: 1481 (2001)). Consistent with this structural similarity, compound I' was capable of destabilizing at least a portion of authentic PHF. These data suggest that despite the presence of substantial microheterogeneity, the tau-tau interactions appearing in authentic tau filaments are recapitulated in fatty-acid induced tau filaments. As a result, the in vitro system described here will be useful for developing additional tau filament antagonists with potentially greater affinity and selectivity.

The inhibitors suitable for use in the present invention are selected from the group consisting of (1) a first compound of the general formula

I wherein $R_1$ is an aliphatic radical having one to six carbon atoms and wherein $R_2$ and $R_3$ independently are a second aliphatic radical having one to six carbon atoms, a hydroxyl-substituted aliphatic radical having one to six carbon atoms, or a pheny radical; (2) a second compound of general formula

II wherein $R_4$, $R_6$, and $R_8$ are independently a third aliphatic radical having 1 to 6 carbon atoms and $R_5$ and $R_7$ are independently a fourth aliphatic radical having 1 to 6 carbon atoms or a second hydroxyl-substituted aliphatic radical having one to six carbon atoms; (3) a third compound of general formula

III

(4) a fourth compound of general formula

IV wherein $R_9$ and $R_{10}$ independently are a fourth aliphatic radical having 1 to 6 carbon atoms; (5) a fifth compound of general formula

V wherein $R_{11}$ is a carboxylic acid-substituted aliphatic radical having 1 to 6 carbon atoms and $R_{12}$ is a fifth aliphatic radical having 1 to 6 carbon atoms; and (6) pharmaceutically acceptable salts thereof. Mixtures of such inhibitors can also be used.

In the above formulae I, II, IV, and V, $R_1$, $R_4$, $R_6$, $R_8$, $R_9$, $R_{10}$, and $R_{11}$ are independently alkyl radicals having 1 to 6 carbon atoms. Examples of such alkyl or aliphatic radicals are methyl, ethyl, propyl, butyl, pentyl, and hexyl, including both straight and branched radicals. Preferably the alkyl radicals are methyl or ethyl and more preferably methyl.

In the above formula I, $R_2$ and $R_3$ are independently alkyl or aliphatic radicals having 1 to 6 carbon atoms, hydroxyl-substituted alkyl or aliphatic radicals having 1 to 6 carbon atoms, or phenyl radicals. Examples of such alkyl or aliphatic radicals are methyl, ethyl, propyl, butyl, pentyl, and hexyl radicals, including both straight and branched radicals. Preferably the alkyl radicals are methyl or ethyl and more preferably methyl. Examples of such hydroxyl-substituted alkyl or al iphatic radicals are hydroxyl-substituted methyl, ethyl, propyl, butyl, pentyl, and hexyl, including both straight and branched radicals. Preferably the hydroxyl-substituted alkyl radicals are —$(CH_2)_nCH_2OH$ radicals where n is an integer 0 to 5; more preferably n is 1.

In the above formula II, $R_5$ and $R_7$ are independently alkyl or aliphatic radicals having 1 to 6 carbon atoms or hydroxyl-substituted alkyl or aliphatic radicals having 1 to 6 carbon atoms. Examples of such alkyl or aliphatic radicals are methyl, ethyl, propyl, butyl, pentyl, and hexyl radicals, including both straight and branched radicals. Preferably the alkyl radicals are methyl or ethyl and more preferably methyl. Examples of such hydroxyl-substituted alkyl or aliphatic radicals are hydroxyl-substituted methyl, ethyl, propyl, butyl, pentyl, and hexyl, including both straight and branched radicals. Preferably the hydroxyl-substituted alkyl radicals are —$(CH_2)_nCH_2OH$ radicals where n is an integer 0 to 5; more preferably n is 1.

In the above formula V, $R_{11}$ is a carboxylic acid alkyl or aliphatic radical having 1 to 6 carbon atoms. Examples of such carboxylic acid-substituted alkyl or aliphatic radicals are carboxylic acid-substituted methyl, ethyl, propyl, butyl, pentyl, and hexyl, including both straight and branched radicals. Preferably the carboxylic acid-substituted alkyl radicals are —$(CH_2)_nCH_2COOH$ radicals where n is an integer 0 to 5; more preferably n is 2.

These inhibitors were identified using essentially the methods described in co-pending U.S. application Ser. No. 09/919,475, filed on the same date as the present application and based on U.S. Provisional Application Serial No. 60/221,777 filed on Jul. 21, 2000. These inhibitors are specific relatively low molecular weight liqands which inhibit and/or reverse tau filament formation or polymerization. This co-pending application, which is owned by the same assignee of the present application, is hereby incorporated by reference. These liqands or inhibitors can be used therapeutically to treat certain neurological disorders or disease states, including Alzheimer's disease, in which tau filaments are formed.

Preferably, the inhibitor is the first compound of the general formula

I wherein $R_1$ is an aliphatic radical having one to six carbon atoms and wherein $R_2$ and $R_3$ independently are a second aliphatic radical having one to six carbon atoms, a hydroxyl-substituted aliphatic radical having one to six carbon atoms, or a pheny radical. More preferably, the inhibitor is 2-[[4-(dimethylamino)phenyl]azo]-6-methoxylbenzothiazole (i.e., $R_1$, $R_2$, and $R_3$ are methyl groups in the above formula I; compound I'); this preferred inhibitor inhibited arachidonic acid polymerization of full length tau protein at substoichiometric concentrations relative to tau (1:40 molar ratio) with an $IC_{50}$ of about 60 nM. Specific examples of other inhibitors of general formula I include [4-(6-methoxy-benzothiazol-2-ylazo)phenyl]-methylphenyl amine (i.e., $R_1$ and $R_2$ are methyl radicals and $R_3$ is phenyl) which has an $IC_{50}$ of about 60 nM; 2-[[4-(N-ethyl-N-β-hydroxyethyl amino)phenyl]azo]-6-methoxybenzothiazole (i.e., $R_1$ is methyl, $R_2$ is 2-hydroxyethyl, and $R_3$ is ethyl) which has an $IC_{50}$, of about 60 nM; and 2-[[4-(didethylamino)phenyl] azo]-6-methoxybenzothiazole (i.e., $R_1$ is methyl, and $R_2$ and $R_3$ are ethyl radicals) which has an $IC_{50}$ of about 60 nM.

Other inhibitors include compounds of general formula II above. More preferably, in general formula II $R_4$ and $R_8$ are methyl radicals, $R_5$ and $R_7$ are —$(CH_2)_2OH$, and $R_6$ is ethyl. Thus, the preferred inhibitor of general formula II is 3-(2-hydroxy-ethyl)-2-{2-[3-(2-hydroxyl-ethyl)-5-methoxy-3H-benzothiazol-2-ylidenemethyl]-but-1-enyl}-5-methoxy-benzothiazol-3-ium. More preferably, an iodide salt of this inhibitor is employed; the idodide salt of this preferred inhibitor has an $IC_{50}$ of about 40 nM.

Another inhibitor is the compound of formula III above. Compound III is 3-hydroxy-napthalene-2-carboxylic acid (2-oxo-1,2-dihydro-indol-3-ylidene)-hydrazide and has an $IC_{50}$ of about 600 nM.

Other inhibitors of this invention include compounds of general formula IV. A preferred inhibitor of general formula IV is 3-[4'-(3-carboxy-2-hydroxy4-methyl-cyclohexa-1,5-dienylazo)-biphenyl-4-ylazo]-2-hydroxy-6-methyl benzoic acid (i.e., $R_9$ and $R_{10}$ are methyl radicals) which has an $IC_{50}$ of about 400 nM.

Other inhibitors of this invention include compounds of general formula V. A preferred inhibitor of general formula V is 4-[3-(2-hydroxy-naphthalen-1-ylazo)-5-methyl-thiophen-2-yl]-butyric acid (i.e., $R_{11}$ is —$(CH_2)_3COOH$ and $R_{12}$ is a methyl radical) which has an $IC_{50}$ of about 700 nM.

In one especially preferred embodiment, the mammal is a human. Generally the inhibitor is administered in an effective amount which can be determined using conventional techniques. Generally, the inhibitor is administered in an amount selected from about 10 mg per day to about 1000 mg per day.

The inhibitors of the present invention may also administered in combination with other inhibitors of fatty acid oxidation (i.e., co-inhibitors), including, for example, vitamins with antioxidative properties, non-steroidal anti-inflammatory drugs (NSAIDS), and selective inhibitors of cyclooxygenase-2. Examples of suitable vitamins with antioxidative properties include, but is not limited to, vitamin E, beta carotene, and vitamin C. Examples of suitable non-steroidal anti-inflammatory drugs include, but is not limited to, aspirin, dilofenic, and ibuprofen. In another embodiment, the inhibitor of fatty acid oxygenation is a selective inhibitor of cyclooxygenase-2. These co-inhibitors, if used, are generally administered at about 1000 mg per day to about 2500 mg per day.

In one embodiment, the administering of the inhibitors of this invention is performed repeatedly over a period of at least one week. In one embodiment, the administering is performed repeatedly over a period of at least one month. In one embodiment, the administering is performed repeatedly over a period of at least three months. In one embodiment, the administering is performed repeatedly over a period of at least one year. In another embodiment, the administering is performed at least once monthly. In another embodiment, the administering is performed at least once weekly. In another embodiment, the administering is performed at least once daily. In another embodiment, the administering is performed at least once weekly for at least one month. In another embodiment, the administering is performed at least once per day for at least one month.

This aspect of the invention provides for treatment and/or prevention of various diseases and disorders associated with induction of tau polymerization by oxidized fatty acids. The invention provides methods of treatment (and prophylaxis) by administration to a subject of an effective amount of a therapeutic of the invention. In a preferred aspect, the therapeutic is substantially purified. The patient or subject is preferably an animal, including, but not limited to, cows, pigs, horses, chickens, cats, dogs, and the like, and more preferably is a mammal, and most preferably is a human.

Various delivery systems are known and can be used to administer a therapeutic of the invention. Such systems include, for example, encapsulation in liposomes, microparticles, microcapsules, recombinant cells capable of expressing the therapeutic (see, e.g., Wu and Wu, "Receptor-mediated in vitro gene transformation by a soluble DNA carrier system," *J. Biol. Chem.* 262:4429 (1987)), construction of a therapeutic nucleic acid as part of a retroviral or other vector, and the like. Methods of introduction include, but are not limited to, intradermal, intramuscular, intraperitoneal, intravenous, subcutaneous, intranasal, epidural, and oral routes. The therapeutics may be administered by any convenient route, including, for example, infusion or bolus injection, absorption through epithelial or mucocutaneous linings (e.g., oral mucosa, rectal and intestinal mucosa, and the like) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed (e.g., by an inhaler or nebulizer) using a formulation containing an aerosolizing agent.

In a specific embodiment, it may be desirable to administer the pharmaceutical compositions of the invention locally to the area in need of treatment, such as the brain. This may be achieved by, for example, and not by way of limitation, local infusion during surgery, topical application (e.g., wound dressing), injection, catheter, suppository, or implant (e.g., implants formed from porous, non-porous, or gelatinous materials, including membranes, such as sialastic membranes or fibers), and the like. In one embodiment, administration can be by direct injection at the site (or former site) of a tissue that is subject to damage by oxidation, such as the brain. In another embodiment, the therapeutic can be delivered in a vesicle, in particular a liposome (see, e.g., Langer, "New methods of drug delivery," *Science* 249:1527 (1990); Treat et al., in *Liposomes in the Therapy of Infectious Disease and Cancer*, Lopez-Berestein and Fidler (eds.), Liss, N.Y., pp. 353–365 (1989)).

In yet another embodiment, the therapeutic can be delivered in a controlled release system. In one embodiment, a pump may be used (see, e.g., Langer, (1990); Sefton, "Implantable pumps," *Crit. Rev. Biomed. Eng.* 14: 201 (1987); Buchwald et al., "Long-term, continuous intravenous heparin administration by an implantable infusion pump in ambulatory patients with recurrent venous thrombosis," *Surgery* 88: 507 (1980); and Saudek et al., "A preliminary trial of the programmable implantable medication system for insulin delivery," *N. Engl. J. Med.* 321: 574 (1989)). In another embodiment, polymeric materials can be used (see, e.g., Ranger et al., *Macromol. Sci. Rev. Macromol. Chem.* 23: 61 (1983); Levy et al., "Inhibition of calcification of bioprosthetic heart valves by local controlled-release diphosphonate," *Science* 228:190 (1985); During et al., "Controlled release of dopamine from a polymeric brain implant: in vivo characterization," *Ann. Neurol.* 25: 351 (1989); and Howard et al., "Intracerebral drug delivery in rats with lesion-induced memory deficits," *J. Neurosurg.* 71: 105 (1989)). Other controlled release systems discussed in the review by Langer et al. (1990) can also be used.

Generally the inhibitors of this invention typically are administered using a pharmaceutically acceptable carrier. The term "pharmaceutically acceptable" means approved by a regulatory agency of the federal or a state government or listed in the U.S. Pharmacopeia or other generally recognized pharmacopeia for use in animals, and, more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable, or synthetic origin, such as peanut oil, soybean oil, mineral oil, sesame oil, and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The therapeutic, if desired, can also contain minor amounts of wetting or emulsifying agents, or pH buffering agents. These therapeutics can take the form of solutions, suspensions, emulsion, tablets, pills, capsules, powders, sustained-release formulations, and the like. The therapeutic can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. Examples of suitable pharmaceutical carriers are described in "Remington's Pharmaceutical Sciences" by E. W. Martin. Such therapeutics will contain a therapeutically effective amount of the active ingredient, preferably in purified form, together with a suitable amount of carrier so as to provide proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampule of sterile water or saline can be provided so that the ingredients may be mixed prior to administration.

The amount of the therapeutic of the invention which will be effective depends on the nature of the tau-related disorder or condition, as well as the stage of the disorder or condition. Effective amounts can be determined by standard clinical techniques. In addition, in vitro assays, such as those described below, may optionally be employed to help identify optimal dosage ranges. The precise dose to be employed in the formulation will also depend on the route of administration, and should be decided according to the judgment of the health care practitioner and each patient's circumstances. However, suitable dosage ranges are about 10 mg/day to about 1000 mg/day. Effective doses may be extrapolated from dose-response curves derived from in vitro or animal model test systems. The invention also provides a pharmaceutical pack or kit comprising one or more containers filled with one or more of the ingredients of the therapeutics of the invention.

In one embodiment, the method for regulating the assembly of the protein tau in the brain of a patient comprises:

identifying a patient in need of a method for inhibiting tau polymerization in the brain; and administering to the patient a pharmacologically effective amount of an inhibitor of fatty acid oxidation of formula I, II, III, IV, or V as defined herein.

In one embodiment, the identifying being based on identifying mutant genomic subtypes of tau in the patient. Typically, these mutant subtypes are involved with increased Tau protein polymerization. See review by Spillantini et al., Trends in Neurosciences, 21: 428 (1998). In another embodiment, the identifying is other than a diagnosis of Alzheimer's disease. For this embodiment, the identifying may be, but is not limited to, the diagnosis of another disorder involving tau polymerization, such as Pick's disease, progressive supranuclear palsy, corticobasal degeneration and familial frontotemporal dementia, and parkinsonism linked to chromosome 17 (FTDP-17).

The following example describes and illustrates the methods and compositions of the invention. This example is intended to be merely illustrative of the present invention, and not limiting thereof in either scope or spirit. Unless indicated otherwise, all percentages are by weight. Those skilled in the art will readily understand that variations of the materials, conditions, and processes described in the example can be used.

EXAMPLE

Materials. Recombinant htau40 and double mutant htau40$^{C291A, C322A}$ were expressed and purified as described previously (Carmel et al., *J. Biol. Chem.* 271, 32789 (1996); Gamblin et al., *Biochemistry* 39, 14203 (2000); co-pending U.S. application Ser. No. 09/919,475, filed on the same date as the present application and based on U.S. Provisional Application Serial No. 60/221,777 filed on Jul. 31, 2000). Stock solutions of $A\beta_{1-40}$ (Bachem; Philadelphia, Pa.) were prepared in DMSO and filtered (0.2 mm cutoff) prior to use. Thioflavin S (Sigma; St. Louis, Mo.) was prepared in water (10 mM) assuming an approximate molecular mass of 650 daltons. Arachidonic acid (Fluka; Milwaukee, Wis.) was reconstituted in 100% ethanol and stored under argon gas at −80° C. until used. Tau polymerization inhibitor 2-[[4-(dimethylamino)phenyl]azo]-6-methoxybenzothiazole. (Neuronautics, Inc.; Evanston, Ill.) was dissolved and stored at −20° C. in DMSO. AD-derived tau filaments were prepared (Ksiezak-Reding et al., *Neurobiol. Aging* 15: 11 (1994)) and stored at about 1 mg/ml concentration at −20° C. until used.

Tau Polymerization. Purified isoforms of tau were polymerized as described previously (Wilson et al., *Am. J. Pathol.* 150: 2181 (1997); King et al., *Biochemistry* 38: 14851 (1999); King et al., *J. Neurochem.* 74: 1749 (2000)). Briefly, 2–8 mM (final concentration) htau40 or mutant htau40$^{C291A, C322A}$ was incubated at room temperature in the presence or absence of 2-[[4-(dimethylamino)phenyl]azo]-6-methoxylbenzothiazole (compound I') with polymerization buffer (10 mM 4-[2-hydroxyethyl]-1-piperazineethanesulfonic acid, 100 mM NaCl, and 5 mM DTT) containing 4 mM thioflavin S. Polymerization was induced by the addition of arachidonic acid (75–100 mM) and continued until analyzed by fluorescence or electron microscopy assays described below. When present, compound I' final concentration varied from 0.05–2 mM. Control reactions were normalized for DMSO vehicle, which was limited to 5% in all reactions.

Tau Depolymerization. Solutions of purified htau40 or htau40$^{C291A, C322A}$ (8 mM) were polymerized as described above for 3.5 hours. To assay dilution-mediated depolymerization, aliquots (50 ml) of reaction product were injected into a stirred quartz cuvette containing 1 ml of polymerization buffer with 4 mM thioflavin S and fluorescence decay followed as a function of time (room temperature). When present, arachidonic acid was 50 mM and tau was held at 2 mM.

To assay inhibitor-mediated depolymerization, compound I' was added to polymerized tau to a final concentration of 0.2 mM into two separate microcentrifuge tubes. Aliquots were removed from each sample after 10, 20, 30, 45, 60 minutes incubation and subjected to fluorescence or electron microscopy assays described below. Control (no compound I') reactions were normalized for DMSO vehicle, which was limited to 5% in all reactions.

The ability of compound I' (2 mM) to depolymerize authentic filaments (0.033 mg/ml) was assayed as above except that timepoints were limited to 0, 10, and 20 min post addition.

Fluorescence. Tau aggregation and disassembly were monitored by following thioflavin S fluorescence as described previously (King et al., 1999). Inhibitory activity of compound I' was quantified by fitting the resultant data to the relationship $$A = A_0 + (A_{max} - A_0)/[1 + 10^{(\log IC50 - \log X)}]$$

where A and $A_0$ are blank-adjusted fluorescence in the presence and absence of inhibitor (at concentration X), respectively. $IC_{50}$ values were calculated using the nonlinear regression algorithm of GRAPHPAD PRISM (GraphPad Software Inc.).

Transmission Electron Microscopy. Aliquots (50 ml) of polymerization and depolymerization reactions were removed, fixed with glutaraldehyde (2%), and adsorbed (1 min) onto 300 mesh formvar/carbon-coated copper grids (Electron Microscopy Sciences; Ft. Washington, Pa.). The resultant grids were washed with water, stained (1 min) with 2% uranyl acetate (Electron Microscopy Sciences), washed again with water, blotted dry, and viewed in a Phillips CM 12 microscope operated at 65 kV. Four to six random images from each experimental condition were captured on film at either 13,000× or 22,000× magnification, digitized, calibrated, and imported into Optimas 6.5.1 for quantitation of filament length and number as described previously (King et al., 2000). Individual filaments defined as any object greater than 50 nm in its long axis were counted manually. Counts from each of the 4 to 6 random images per condition are reported as an average±standard deviation for both filament length and number. Length distributions were quantified in 100 nm-wide bins, beginning with 50–150 nm lengths and continuing 151–250 nm, 251–350 nm, etc.

$A\beta_{1-40}$ Aggregation. Stock solutions of $A\beta$ (1 mM) were prepared in DMSO and filtered (0.2 mM cutoff). Aggregation was initiated by diluting the $A\beta b$ stock solution to 20 mM final concentration in aggregation buffer (150 mM NaCl, 10 mM 2-[N-morpholino]ethanesulfonic acid, pH 6.2; final volume 100 mL). Turbidity resulting from $A\beta$ aggregation in the presence (20 mM final concentration) and absence of compound I' was monitored as a function of time in a Beckman DU640B spectrophotometer at 350 nm versus a DMSO vehicle blank (Snyder et al., *Biophys. J.* 67: 1216 (1994); Evans et al., *Proc. Natl. Acad. Sci. USA* 92: 763 (1995)). Cuvettes were rapidly inverted before each reading. Total DMSO vehicle concentration was controlled among samples and did not exceed 5% (v/v).

Results for Compound I'

Inhibition of tau Polymerization. To identify chemical antagonists of tau polymerization, a library of small molecules (containing approximately 6000 organic compounds<about 700 Da consisting primarily of carbon, hydrogen, oxygen, nitrogen, and sulfur) was screened for inhibitory activity against htau40 (2 mM) assembly induced by arachidonic acid (50 mM) under near-physiological conditions using the methods described in co-pending U.S. application Ser. No. 09/919,475, filed on the same date as the present application and based on U.S. Provisional Application Serial No. 60/221,777 filed on Jul. 31, 2000. 2-[[4-(Dimethylamino)phenyl]azo]-6-methoxylbenzothiazole (compound I'), an uncharged (at physiological pH) member of the azo dye family that includes Congo Red, was identified as having inhibitory activity against htau40.

Figure 1:
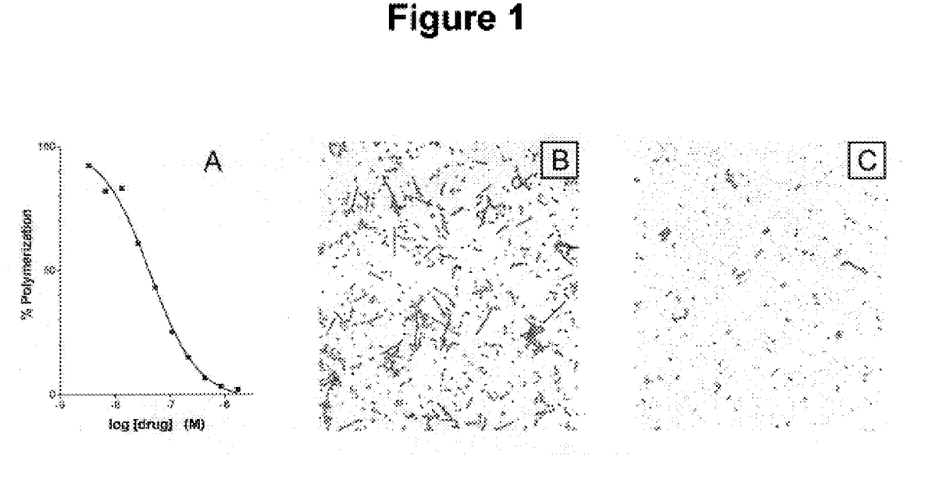

The effect of compound I' on polymerization of htau40 (2 mM) was quantified using a thioflavin S (2–4 mM) fluorescence assay (King et al., 1999). Compound I' inhibited thioflavin S fluorescence in a dose dependent manner with an $IC_{50}$ of 54±6 nM (FIG. 1, Panel A). All inhibition isotherms showed no sign of cooperativity and were consistent with occupancy of a single inhibitory binding site. These data suggested that compound I' is a potent inhibitor of tau polymerization, being active at substoichiometric concentrations relative to tau protomer, arachidonic acid inducer, and thioflavin S probe.

To confirm these findings, inhibition of tau filament formation was observed directly by transmission electron microscopy (King et al., 2000). An htau40 mutant devoid of Cys residues (htau40$^{C291A, C322A}$, as described in co-pending U.S. application Ser. No. 09/919,745, filed on the same date as the present application and based on U.S. Provisional Application Serial No. 60/221,777 filed on Jul. 31, 2000) was employed for this experiment for two reasons. First, it yielded an exponential population of filaments with greater occupancy of long filament bins, which simplified quantitation of filament lengths (Gamblin et al., *Biochemistry* 39: 14203 (2000)). Second, the lack of Cys residues eliminated possible covalent modification of protein by compound I'. Thus this potential complication, which had been observed with aromatic inhibitors of tubulin polymerization (Combeau et al., *Mol. Pharmacol.* 57: 553 (2000)), was avoided. When incubated under standard conditions with or without thioflavin S (4 mM), htau40$^{C291A, C322A}$ (8 mM) formed abundant straight filaments over a 3 hour period (FIG. 1, Panel B). In the presence of compound I' (200 nM; 1:40 molar stoichiometry with respect to tau protomer), however, polymerization as measured by either the total number or length of all filaments typically decreased to 10–20% of control values (FIG. 1, Panel C). These results confirmed that compound I' was an inhibitor of tau polymerization and was not acting as a mere competitive binding antagonist of the thioflavin S probe.

Compound I' Promotes tau Disaggregation. Other members of the azo dye family have been shown to bind fibrils composed of different protein protomers such as amyloid beta peptide, insulin, or prion protein (Klunk et al., *J. Histochem. Cytochem.* 37:1273 (1989); Ashburn et al., *Chem. Biology* 3: 351 (1996)). In some examples, the dyes were capable of antagonizing fibril formation from protomer (Lorenzo et al., *Proc. Natl. Acad. Sci. USA* 91: 12243 (1994); Rudyk et al., *J. Gen. Virol.* 81: 1155 (2000)). It has been postulated that in these examples they act either by (1) lowering the effective monomer concentration; (2) blocking growth at filament ends; or (3) increasing the rate of filament breakage (Masel et al., *Biophys Chem.* 88: 47 (2000)). In the case of compound I', 50% inhibition of tau polymerization was observed at 1:40 molar stoichiometry (compound I':tau) suggesting that it cannot act solely by lowering the concentration of tau monomer. Therefore the ability of compound I' to block and potentially depolymerize or fragment mature synthetic filaments was examined in detail.

Figure 2:
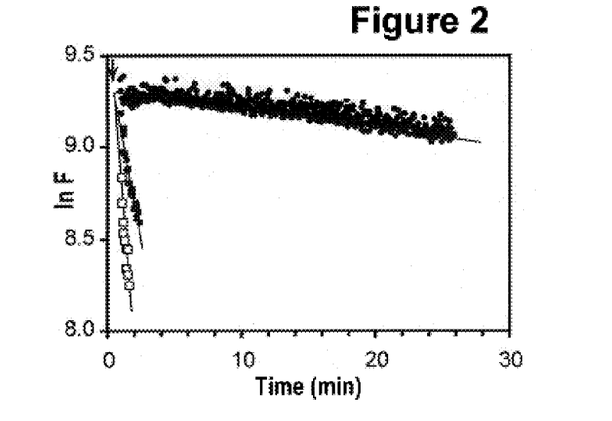

The reversibility of tau polymerization in the absence of compound I' was first demonstrated by dilution experiments. Htau40 was incubated under polymerization conditions for 3 hours at room temperature and then diluted into assembly buffer. Subsequent loss of tau polymer by mass action was then followed by thioflavin S fluorescence over time (King et al., 1999). When diluted 20-fold into assembly buffer alone, thioflavin S fluorescence rapidly decayed with an initial first order rate of 0.83 min$^{-1}$ (FIG. 2). Dilution into assembly buffer containing 2 mM protomer (i.e., recombinant htau40 above the critical concentration for assembly; King et al., 1999) slowed the decay rate only modestly to 0.39 min$^{-1}$. In contrast, dilution into buffer containing 50 mM arachidonic acid slowed decay to 0.0085 min$^{-1}$; 50-fold slower than dilution in buffer alone. These data show that tau polymerization is reversible, and confirm that the presence of both protomer and arachidonic acid is necessary to ensure stability of mature synthetic filaments when working with purified recombinant tau protein.

To determine whether compound I' also could destabilize mature filaments and mimic the depolymerization observed in dilution experiments, tau filaments assembled in the presence of thioflavin S for 3 hours under standard conditions were incubated in the presence or absence of compound I' (200 nM) and examined after various times by electron microscopy and fluorescence. Dose response curves again showed an inhibition pattern consistent with a single binding site and an $IC_{50}$ of 91±13 nM (data not shown). Together these data show that compound I' inhibits further growth and promotes disassembly of synthetic tau filaments at substoichiometric concentrations in the presence of 8 mM protomer (htau40) and 75 mM arachidonic acid inducer.

Mechanism of Ligand-Mediated Depolymerization. The kinetic characteristics of endwise depolymerization of linear protein assemblies at equilibrium depends on the length distribution of polymers (Kristofferson et al., *J. Biol. Chem.* 255: 8567 (1980)). For tau filaments, which adopt a near exponential distribution of lengths (Wilson et al., J. Biol. Chem. 270: 24306 (1995); Gamblin et al., *Biochemistry* 39: 14203 (2000)), dissociation rates are predicted to be first order (Kristofferson et al., 1980). Moreover, filament disassembly is predicted to proceed while maintaining an exponential distribution of gradually shortening filaments lengths (Kristofferson et al., 1980).

Figure 3:
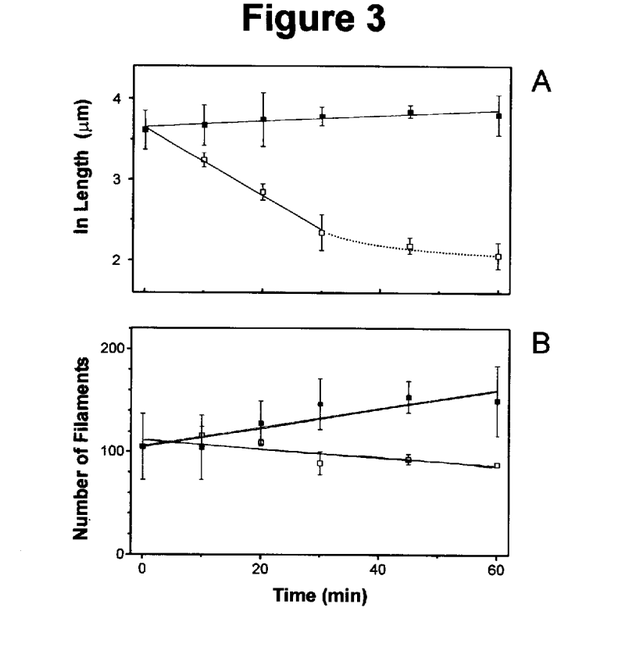

To determine whether compound I'-mediated tau depolymerization proceeded by an endwise mechanism, htau40$^{C291A, C322A}$ (4 mM) was polymerized over a 3.5 hour period after which time compound I' (200 nM) or DMSO vehicle alone was added and filament lengths were measured over a 1 hour "chase" by electron microscopy. In the absence of compound I', total htau40$^{C291A, C322A}$ filament length and number increased modestly over this time period (FIG. 3), consistent with the reaction approaching equilibrium (Gamblin et al., *Biochemistry* 39: 6136 (2000)). In contrast, addition of compound I' (200 nM) led to a decrease in total filament length over 30 min until a new equilibrium was achieved. The initial rate of filament loss was well modeled as a first order decay ($r^2$=0.996; k=0.042 min$^{-1}$) under these conditions (4 mM htau40$^{C291A, C322A}$ and 75 mM arachidonic acid).

Figure 4:
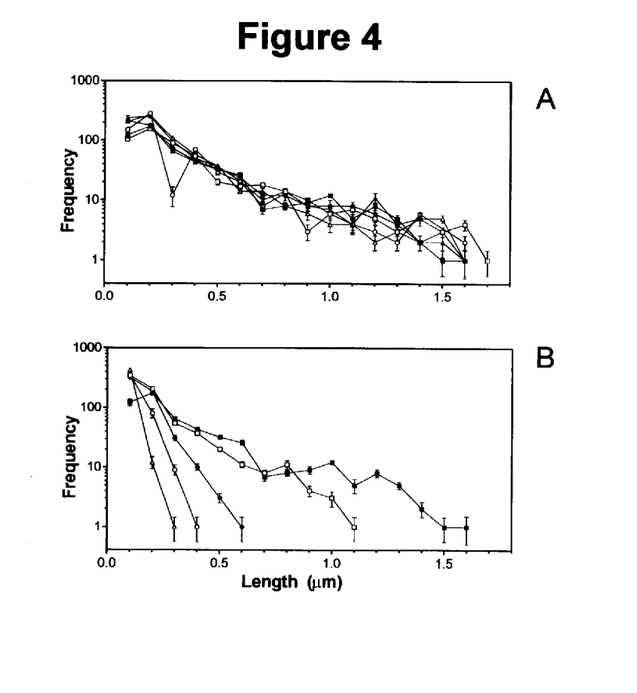

The observation of first order ligand-induced filament depolymerization along with substoichiometric activity suggested that compound I' promoted sequential release of tau protomers from filament ends rather than random filament breakage. To confirm this hypothesis, the number and length distribution of tau polymers also were examined after treatment of preassembled tau filaments with compound I'. These data showed that compound I'-mediated depolymerization was accompanied by a slow decrease in the number of filaments>50 nm in length, which is inconsistent with the random breakage-mediated depolymerization model (FIG. 3). Moreover, an exponential polymer length distribution was maintained throughout the compound I'-mediated depolymerization reaction as the filaments shifted to shorter lengths (FIG. 4). Together these data suggest that at substoichiometric concentrations, compound I' treatment leads to endwise filament depolymerization.

Figure 5:
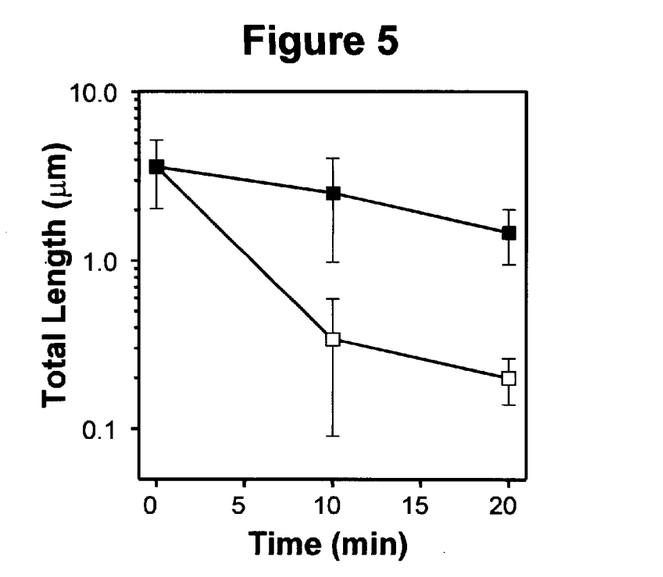

Authentic PHF Disassembly. In contrast to synthetic tau filaments created from recombinant protomer, authentic tau filaments consist of multiple tau isoforms in different states of postranslational modification (Buee et al., *Brain Res Rev.* 33: 95 (2000)). To determine whether compound I' could also promote disassembly of authentic filaments, PHFs prepared from an AD brain by differential centrifugation were incubated alone or in the presence of compound I' (2 mM) and followed over time by electron microscopy. In the absence of compound I', authentic filaments partially depolymerized over a 20 min period. Thus while being far more stable than fresh synthetic htau40 filaments, at least a portion of the authentic filament population appeared capable of disassembly over a 20-minute time course. In the presence of compound I', depolymerization was greatly enhanced, and led to decreases in total filament length to between 10–50% of control (FIG. 5). These data suggest that the interactions between tau filaments and compound I' are conserved in both authentic and synthetic filaments, and that compounds such as compound I' may be capable of antagonizing filament formation in vivo.

Figure 6:
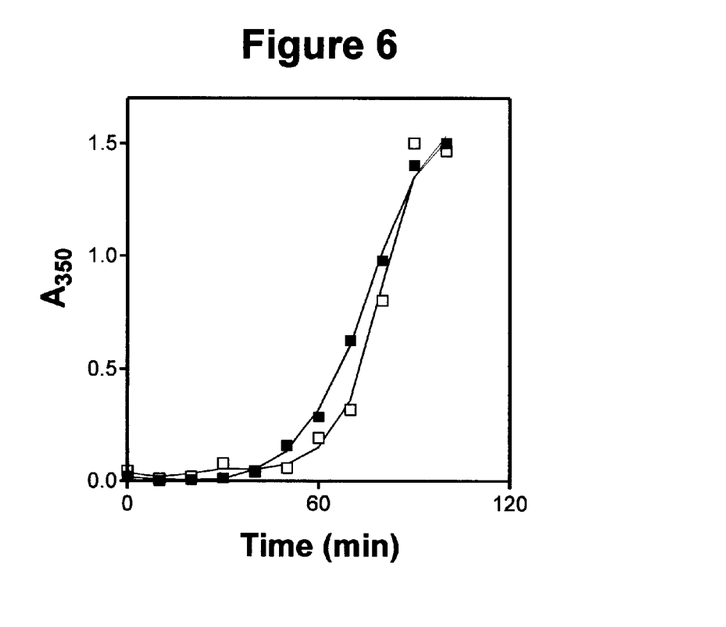
FIG. 6. This figure illustrates that compound I' is selective for tau polymerization. Aβ (20 μM) was incubated in assembly buffer in the presence of DMSO vehicle (■) or 20 μM compound I' (□). The resultant assembly reaction was followed by absorbance at 350 nm. Compound I' did not inhibit Aβ polymerization under these conditions.

Selectivity of tau Polymerization Antagonism. Like other azo dyes, compound I' has been shown to bind a variety of amyloid aggregates at low micromolar concentrations, including those formed from Aβ and insulin (Caprathe et al., U.S. Pat. No. 6,001,331 (Dec. 14, 1999)). To determine whether amyloid binding was accompanied by polymerization inhibitory activity, the ability of compound I' to inhibit spontaneous Aβ$_{1-40}$ assembly was examined. In the absence of ligand, Aβ$_{1-40}$ (20 mM) polymerized spontaneously after a lag of 1 hour (FIG. 6). The presence of compound I' at concentrations that were stoichiometric with respect to Aβ$_{1-40}$ protomer (20 mM) and nearly an order of magnitude above the published binding constant did not alter Aβ$_{1-40}$ assembly kinetics significantly (FIG. 6). These data indicate that, at least in the case of Aβ$_{1-40}$, it is possible to segregate the binding activity of compound I' from its polymerization inhibition activity. Furthermore, these data confirm that despite similarities in polymer structures (i.e., extended β-sheet) formed from different protein protomers, it is possible to select small ligands such as compound I' with target-selective binding and assembly inhibition activity.

Other compounds. Compounds I, II, III, IV, and V were identified using similar techniques as discussed above for Compound I'.

Throughout this application, various patents, publications, books, and nucleic acid and amino acid sequences have been cited. The entireties of each of these patents, publications, books, and sequences are hereby incorporated by reference into this application.

What is claimed is:

1. A method for regulating the assembly of the protein tau in the brain of a patient, comprises:

identifying a patient in need of a method for inhibiting tau polymerization in the brain; and administering to the patient a pharmacologically effective amount of an inhibitor of fatty acid oxidation, wherein the inhibitor is selected from the group consisting of (1) a first compound of the general formula I wherein $R_1$ is an aliphatic radical having one to six carbon atoms and wherein $R_2$ and $R_3$ independently are a second aliphatic radical having one to six carbon atoms, a hydroxyl-substituted aliphatic radical having one to six carbon atoms, or a pheny radical; (2) a second compound of general formula II wherein $R_4$, $R_6$, and $R_8$ are independently a third aliphatic radical having 1 to 6 carbon atoms and $R_5$ and $R_7$ are independently a fourth aliphatic radical having 1 to 6 carbon atoms or a second hydroxyl-substituted aliphatic radical having one to six carbon atoms; (3) a third compound of general formula III (4) a fourth compound of general formula IV wherein $R_9$ and $R_{10}$ independently are a fourth aliphatic radical having 1 to 6 carbon atoms; (5) a fifth compound of general formula V wherein $R_{11}$ is a carboxylic acid-substituted aliphatic radical having 1 to 6 carbon atoms and $R_{12}$ is a fifth aliphatic radical having 1 to 6 carbon atoms; and (6) pharmaceutically acceptable salts thereof.

2. The method of claim 1, wherein the inhibitor is the first compound or a pharmaceutically acceptable salt of the first compound.

3. The method of claim 2, wherein $R_1$, $R_2$, and $R_3$ are methyl radicals.

4. The method of claim 2, wherein $R_1$ and $R_2$ are methyl radicals and $R_3$ is a phenyl radical.

5. The method of claim 2, wherein $R_1$ is a methyl radical, $R_2$ is a 2-hydroxyethyl radical, and $R_3$ is an ethyl radical.

6. The method of claim 2, wherein $R_1$ is a methyl radical and $R_2$ and $R_3$ are ethyl radicals.

7. The method of claim 1, wherein the inhibitor is the second compound or a pharmaceutically acceptable salt of the second compound.

8. The method of claim 7, wherein $R_4$ and $R_8$ are methyl radicals, $R_5$ and $R_7$ are 2-hydroxylethyl radicals, and $R_6$ is an ethyl radical.

9. The method of claim 8, wherein the inhibitor is an iodide salt of the second compound.

10. The method of claim 1, wherein the inhibitor is the third compound or a pharmaceutically acceptable salt of the third compound.

11. The method of claim 1, wherein the inhibitor is the fourth compound or a pharmaceutically acceptable salt of the fourth compound.

12. The method of claim 11, wherein $R_9$ and $R_{10}$ are methyl radicals.

13. The method of claim 1, wherein the inhibitor is the fifth compound or a pharmaceutically acceptable salt of the fifth compound.

14. The method of claim 13, wherein $R_{11}$ is —$(CH_2)_3COOH$ and $R_{12}$ is a methyl radical.

15. The method of claim 1, wherein the patient is a human and the pharmacologically effective amount is about 10 to about 1000 mg per day.

16. A method for inhibiting or reversing tau filament formation in the brain of a mammal, said method comprises:
   identifying a mammal in need of a method for inhibiting tau polymerization in the brain; and
   administering to the mammal a pharmacologically effective amount of (1) an inhibitor of fatty acid oxidation of the general formula I wherein $R_1$ is an aliphatic radical having one to six carbon atoms and wherein $R_2$ and $R_3$ independently are a second aliphatic radical having one to six carbon atoms, a hydroxyl-substituted aliphatic radical having one to six carbon atoms, or a pheny radical or (2) a pharmaceutically acceptable salt of the inhibitor.

17. The method of claim 16, wherein the mammal is a human.

18. The method of claim 17, wherein $R_1$, $R_2$, and $R_3$ are methyl radicals.

19. The method of claim 17, wherein $R_1$ and $R_2$ are methyl radicals and $R_3$ is a phenyl radical.

20. The method of claim 17, wherein $R_1$ is a methyl radical, $R_2$ is a 2-hydroxyethyl radical, and $R_3$ is an ethyl radical.

21. The method of claim 17, wherein $R_1$ is a methyl radical and $R_2$ and $R_3$ are ethyl radicals.

22. The method of claim 17, wherein the pharmacologically effective amount is about 10 to about 1000 mg per day.

* * * * *